United States Patent
Zahradnik et al.

[11] Patent Number: 5,719,100
[45] Date of Patent: Feb. 17, 1998

[54] WATER TREATMENT COMPOSITIONS

[76] Inventors: Rudolf Zahradnik, 37, Hermanova 170 00, Prague 7, Czechoslovakia; Bruce Barber, 77, Duck Hill Rd., Duxbury, Mass. 02332

[21] Appl. No.: 854,903

[22] Filed: Mar. 20, 1992

[51] Int. Cl.$^6$ ..................... B01J 20/20
[52] U.S. Cl. ............ 502/417; 201/501; 201/502.1; 252/187.23
[58] Field of Search ............... 210/501, 502.1; 252/187.23; 422/30, 37, 61; 502/417

[56] References Cited

U.S. PATENT DOCUMENTS

| | | | |
|---|---|---|---|
| 3,684,437 | 8/1972 | Callerame | 423/472 |
| 3,828,097 | 8/1974 | Callerame | 423/472 |
| 4,045,553 | 8/1977 | Mitsumori et al. | 210/501 |
| 4,084,747 | 4/1978 | Alliger | 422/37 |
| 4,389,311 | 6/1983 | La Freniere | 422/61 |
| 4,690,722 | 9/1987 | Tell et al. | 252/106 |
| 4,861,514 | 8/1989 | Hutchings | 252/187.21 |
| 4,863,627 | 9/1989 | Davies et al. | 422/28 |
| 4,971,760 | 11/1990 | Rubinstein | 422/37 |
| 5,279,673 | 1/1994 | Dziabo et al. | 422/30 |

OTHER PUBLICATIONS

Rip G. Rice et al., Occurrence of by-Products of Strong Oxidants Reacting with Drinking Water Contaminants-Scope of the Problem Env. Health Pros., vol. 69, pp. 31–44, 1986.
Journal AWWA, A Review of Chlorine Dioxide in Drinking Water Treatment, pp. 62–72, E. Marco et al.
J. Water SRT-Aqua vol. 39, No. 6, pp. 376–386, 1990; Concerns with Using Chlorine-dioxide Disinfection in the USA, B.W. Lykins et al.

*Primary Examiner*—Ivars Cintins

[57] ABSTRACT

Advantageous water treatment compositions are provided, which remain stable prior to their intended use in an aqueous environment. The compositions comprise sodium chlorite and an acid activator. Preferred as an acid activator is citric acid, anhydrous. The composition may also comprise, if desired, activated carbon, which may optionally be ion-impregnated. A method of treating water utilizing the compositions is disclosed, and water treatment kits are also provided.

23 Claims, 4 Drawing Sheets

CHEMICAL CHANGES IN FORMULA A WITH SODIUM CHLORITE INCUBATED IN VEHICLE WITH CITRIC ACID AND SALINE

THE EFFECT OF pH ON NaClO$_2$ DECOMPOSITION TO ClO$_2$

FORMULATION M
10 min - 30 min
after solubilization

WATER TREATMENT COMPOSITIONS

FIELD OF THE INVENTION

The present invention is concerned with providing stable compositions which can be used to treat water through the release of chlorine dioxide. The present invention is also concerned with a convenient and advantageous method of providing treated water (e.g., drinking water).

BACKGROUND OF THE INVENTION

Chlorine dioxide, having a molecular weight 67.46, is one of the few compounds in nature that exists almost entirely as a monomeric free radical. Liquid chlorine dioxide is deep red in color and explosive above −40° F. and its vapor resembles chlorine in appearance and odor. Concentrated chlorine dioxide vapor is also explosive at 5.8 psi (40 kPa) above atmospheric pressure, 6 psig (41 kPa). All attempts to compress and store chlorine dioxide gas, either alone or in combination with other gases, have been commercially unsuccessful. Because of its explosive hazard, chlorine dioxide must be manufactured at the point of use.

The first reported use of chlorine dioxide in preparing drinking water occurred in 1944, at the Niagara Falls, N.Y., water treatment plant. There is a renewed interest in disinfection with chlorine dioxide in the United States because of federal regulations on disinfection by-products. Bench studies and field applications of chlorine dioxide have shown that it is an effective biocide that does not produce halogenated by-products such as trihalomethanes.[1] While there may exist some health concerns with ingesting chlorine dioxide and its metabolites, chlorite, and concerns about tastes and odors, each of these concerns may be alleviated by removing the chlorine-dioxide species with granular activated carbon or reducing them to chloride before water distribution.[2]

U.S. Pat. No. 4,861,514 of Hutchings discloses compositions which release chlorine dioxide in water and which comprise sodium chlorite, an initiator, and water. The sodium chlorite and initiator each being present in the composition in at least an amount adapted to form interactively an antimicrobially effective concentration of chlorine dioxide in the composition, said composition having a viscosity suitable to suspendably retain the chlorine dioxide in the composition. Suitable as an initiator are hydroxy alkylcelluloses having 2 to about 5 carbons in the alkyl group; alkali metal alginates; xanthan; carrageenan; agar; compounds containing an aldehyde substituent group, including perfumes; perfumes not included in the previous class of aldehydic compounds, and dyes. Mixtures of such initiators are also disclosed by Hutchings.

Natural surface waters are utilized to an increasing degree to cover increasing needs for drinking and service water, and humic substances represent a major portion of the organic pollution in natural surface waters.

Depending on their physical and chemical properties, humic acids can be classified as humus acids (humic acids, fulvoacids, hymatomelanic acids), humines and humus coal.[3] of humic substances in natural surface waters, only humic acids are important in water treatment as humines and humus coal are insoluble in water and not hydrolyzable. Since humic acids differ in their solubility in acidic media, basic media and in ethanol, this property can be utilized in the separation of the individual groups. For example, humic and hymatomelanic acids can be precipitated from acidified solutions as dark precipitates, while fulvoacids remain in solution. In contrast to humic acids, hymatomelanic acids are soluble in ethanol.

In practice, it is difficult to isolate the individual groups of humic substances as they do not have precisely defined structures, and moreover, their composition depends on the nature of the natural materials that were decomposed in their formation. Even so, the results of research work have indicated that humic substances are high molecular weight polycyclic compounds containing aromatic and aliphatic components. Hypothetical structural formulae for humic acids and fulvoacids have been given in the literature.[3,4] The presence of a number of functional groups (carboxylic, hydroxylic—phenolic and alcoholic, methoxylic, quinoid) affects their physical and chemical properties. The —COOH and —OH groups lead to acidity, an exchange capacity and weakly polar character, while the presence of quinoid structures together with hydroxyls leads to redox properties.

Humic substances are present in natural surface waters in concentrations from about 10 mg/l to about 120 mg/l, with extreme values (backwaters) of up to about 500 mg/l.[3,5] A concentration of 100 mg/l is considered to be harmful to man. Humic substances are not directly toxic but their presence can considerably decrease the appearance and taste properties of water. The presence of humic substances cannot only effect drinking water but also service waters (e.g., in the textile industry) where products could be damaged by the presence of such substances. An increase in corrosive properties is also associated with the presence of such substances.

The presence of humic substances is also very detrimental in water treatment processes. In commonly employed procedures, increased contents of these substances can lead to a number of difficulties (breakthrough of humic substances and coagulants, high corrosiveness in the treated water and a decrease in water quality in water mains).[8] However, the greatest danger to health comes from the formation of trihalogen-methanes during chlorination.

Harmful compounds can appear in water treatment in the presence of humic substances not only through the action of chlorine, but also through the action of chlorine dioxide and ozone.[6] The reaction between humic acids and chlorine primarily leads to the formation of chloroform, while mono-, di-, and tri-chloroacetonitriles and cyanobutanic acids have also been found. Chloropicrin has even been found in alkaline medium in the presence of nitrites. The action of chlorine dioxide does not produce trihalogenmethanes, but, e.g., benzenepolycarboxylic acids have been found. Ozonation of humic acids leads to splitting of the polymer chains to yield aliphatic acids, ketones and aromatic compounds such as tetra-, penta- and hexachlorobenzene. Ozonation can also lead to release of substances formerly bonded in humate complexes, (e.g., some pesticides and heavy metals).

Consequently, considerable research work has been directed to a search for an effective and economically reasonable procedure for treating humic waters. This subject was studied in detail by Žáček.[4,5,7] He carried out complex studies of humic substances in water, evaluated separation processes and studied optimization of the technology of clarification with ferric and aluminum compounds.[4,5] Vágner et al[8] considered the use of active carbon for the sorption of humic substances and measured the sorption capacity of several types of active carbon. He measured the organic substance content as the chemical oxygen demand, $COD_{Mn}$, in an oxidation by permanganate. Mention is also made of the removal of humic substances using ion-exchangers XAD1, XAD7, XAD8[3] and XAD4[6] or ion-exchangers based on DEAE cellulose[3]. Tested inorganic sorbents included aluminum oxide, silica gel and calcium carbonate[3].

SUMMARY OF THE INVENTION

The present invention provides advantageous compositions which can be used to readily convert a quantity of untreated water into sanitized water which is suitable for drinking or other potable water uses. The compositions possess the ability to release chlorine dioxide in an aqueous environment and yet remain stable until used for their intended purpose. Exemplary of such compositions, but not limiting thereto, are water sanitation tablets such as described in the Detailed Description Section hereof.

The present invention also provides advantageous water treatment compositions which not only release chlorine dioxide in aqueous environments, but which also contain activated carbon for the absorption of humic substances in the waters treated with the inventive compositions. Advantageously, the active carbon is impregnated with a metal containing ion (e.g.,Fe) so as to maximize the absorption of such humic substances.

The present inventive compositions are able to release chlorine dioxide in an aqueous environment, while remaining stable prior to their intended use through the inventors' ability to place both sodium chlorite and an acid activator (e.g., citric acid, anhydrous; ascorbic acid, anhydrous or the like) in a single composition while preventing the sodium chlorite and acid activator from prematurely reacting together.

The present invention is also concerned with a method of providing potable water, which comprises treating water with one or more of the present inventive compositions.

BRIEF DESCRIPTION OF THE DRAWINGS

The present invention will become more fully understood from the detailed description given here and below and the accompanying drawings which are given by way of illustration only, and thus, are not limitative of the present invention, and wherein.

DETAILED DESCRIPTION OF THE INVENTION

Figure 1:
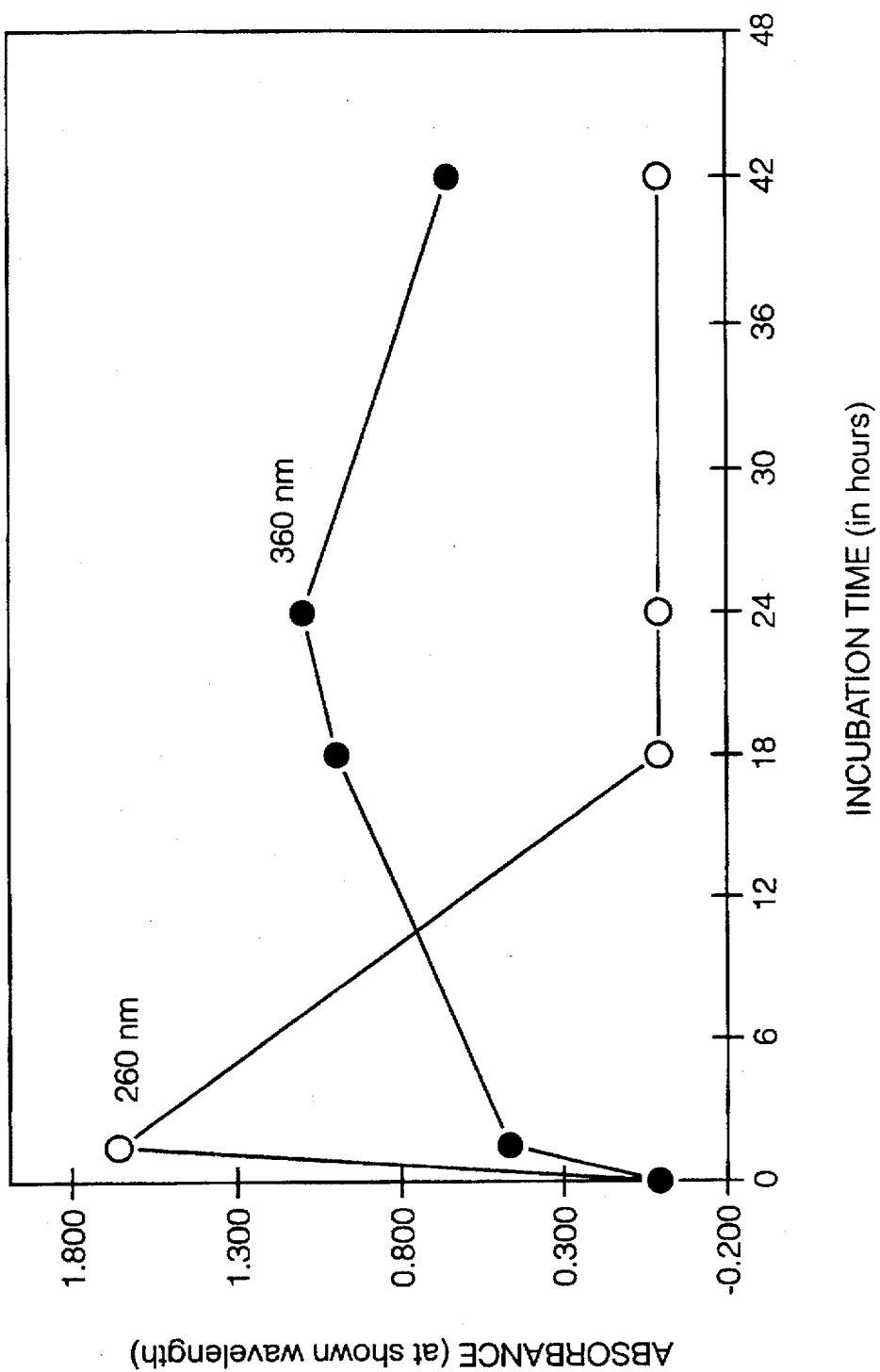
FIG. 1—shows that sodium chlorite decomposes in an aqueous environment of citric acid (pH 3.5) to form chlorine dioxide.

The following Detailed Description is not limiting to the present inventive discovery. Instead, the following description is provided as an aid to those desiring to practice the present invention, since it discloses preferred and advantageous ways in which the present invention can be practiced. It should at all times be understood that minor changes and/or variations can be made in the inventive processes and compositions herein described without departing from the spirit or scope of the present inventive discovery. In this respect, such changes and variations are considered to be those that would be generally and/or readily understood by those of ordinary skill in the art.

The present inventive discovery is only to be limited by the scope of the claims appended hereto, and the equivalents thereof.

Each of the compositions encompassed by the present invention release chlorine dioxide when introduced into an aqueous environment. This release of chlorine dioxide results from the reaction of sodium chlorite with the acid activator (e.g., citric acid, anhydrous USP). In order to simplify the disclosure which occurs below, reference will occasionally be made to the use of sodium chlorite and citric acid in the present inventive composition. Nonetheless, it should be fully understood that the present inventive compositions are not limited to the use of these two specific ingredients, since sodium chlorite can be used in combination with a variety of acid activators to provide a stable composition which releases chlorine dioxide, when introduced into an aqueous environment.

The term "acid activator" as used herein means any physiologically acceptable compound, which can produce a pH in water of at least about 3–4, and which does not unduly and/or adversely effect the taste quality of water at a pH of about 3–4, when said acid containing compound is utilized in one of the present inventive compositions or processes. Exemplary of "acid containing compounds" which can be utilized in the present invention are: citric acid; citric acid, anhydrous; ascorbic acid; ascorbic acid, anhydrous; boric acid; primary sodium phosphate; maleic acid; lactic acid in any of its racemic forms; and the like. The use of citric acid, anhydrous USP as an acid activator is thought especially preferred in the present invention. Whatever the chosen acid activator, it should exist in a powder or granular form at normal temperatures (20°–60° C.) and be physiologically compatible.

The water treatment compositions of the present invention contain sodium chlorite (preferably sodium chlorite, anhydrous). However, since sodium chlorite is inherently unstable and highly active, it is felt preferred that in the present invention the sodium chlorite component be mixed with other substances in the form of a premix, in order to lessen problems of instability and explosiveness. Suitable premixes include those provided in the Example Section thereof, as well as obvious variants thereof. Suitable premixes should have a pH of about 7 to 8 and contain less than about 25% w/w of sodium chlorite therein. Suitable sodium chlorite premixes can be obtained from RIO LINDA CHEMICAL COMPANY, 10th Street, Sacramento, Calif., 95814 if so desired. The use of sodium chlorite premixes in the Example Section hereof does not limit the present invention to the use of premixes, since the use of a sodium chlorite premix is only preferred in the present invention, not required.

The present inventive water treatment compositions are required to remain stable prior to their introduction into an aqueous environment. However, the compositions must contain both the chlorine dioxide precursor, sodium chlorite, and an acid activator. The inclusion of each of these ingredients in a single composition presented problems, since under normal conditions an acid activator and sodium chlorite will explosively react to produce chlorine dioxide. The present inventors have been able to avoid these problems and have been able to incorporate both sodium chlorite and an acid activator in a single composition, while preventing these ingredients from prematurely reacting together.

The inventors' ability to incorporate both an acid activator and sodium chlorite in a single composition, is exemplified herein with a protective coating technique (see Tablets L, M and S), wherein a protective reaction-preventing coat is formed on the sodium chlorite before mixing with the acid activator. Nonetheless, it should be noted that such specific techniques are only illustrative of methods by which compositions of the present invention can be prepared. For example, it is only necessary that one produce a composition containing a reaction-preventing barrier between the sodium chlorite and the acid activator such that the two active ingredients do not react together prematurely (i.e., so that a stable composition is obtained). Such a reaction-preventing barrier could be achieved in a multitude of ways, for example, by microencapsulating or coating one or both of the reactive ingredients, or even through the production of a composition wherein the reactive ingredients are segregated apart from each other (for example, in a multi-layered tablet).

The inventors' ability to prepare the present inventive water treatment compositions also results from their ability to produce compositions containing low residual amounts of moisture therein (less than about 2 to 3% w/w). This is because the release chlorine dioxide from sodium chlorite requires one of two initiators. One of these is moisture (or water), the other is heat (temperatures above about 45°–60° C.). As such, if either one of these conditions is reached prematurely, there can occur a premature release of chlorine dioxide from the present inventive water treatment compositions.

In order to insure that the present inventive compositions maintain a residual amount of moisture therein of below about 2 to 3% w/w, certain procedures should be utilized. First, each component utilized in the present inventive compositions should be tested for moisture (e.g., gravimetrical analysis), and once the moisture thereof is ascertained, the same component should be dried (if needed) to a moisture content below about 0.2 to 0.3% w/w and thereafter be placed in a relatively moisture free environment. Exemplary of such a moisture free environment is a desiccator containing a suitable desiccant, or an environmentally controlled room containing extremely low amounts of moisture therein (e.g., the air therein containing less than 1% w/w moisture). Moreover, when preparing the present inventive compositions, it may be necessary to take precautions such as protecting ingredients from moisture inherently present in the preparer's exhaled breaths (typically containing 80% w/w moisture). Nonetheless, the present inventive compositions, if prepared under suitable conditions, will contain less than about 2 to 3% w/w moisture.

In order to insure that the present inventive compositions contain residual amounts of moisture less than 2 to 3% w/w, the production of the present inventive compositions and packaging thereof should occur under extremely low humidity or moisture conditions. Moreover, the packaged compositions themselves must be capable of remaining moisture free for prolonged periods of time, prior to their intended use. It is fully envisioned that those of ordinary skill in the art will readily recognize procedures which are applicable to the preparation of the present inventive compositions without being unduly burdensome. The use of such techniques to control the moisture content of the present inventive compositions is fully encompassed hereby.

As noted previously, heat can destabilize sodium chlorite (at temperature above about 45°–60° C.). Thus, it is suggested that temperatures above about 45°–60° C. not be utilized in preparing the present inventive compositions whenever sodium chlorite is present therein, since such elevated temperatures can easily cause the release of chlorine dioxide. Even so, preparation of a suitable anhydrous vehicle or acid activator may utilize elevated temperatures, if thereafter, the vehicle or acid activator is allowed to cool before combining sodium chlorite therewith.

The present inventors have discovered that compositions of the present invention, when added to a quantity of water (for example, a liter of water) most preferably should produce a pH in the treated water of about 3–4, in order to assure that an appropriate release of chlorine dioxide occurs in a fast reproducible manner (for example, about 40% in two minutes), so that the water is sanitized. Moreover, while lower pH's (such as 2) can allow for a fast release of chlorine dioxide, the present inventors have discovered that such low pH's can result in water having unpalatable taste characteristics. Conversely, the inventors have also discovered that when compositions of the present invention are added to water so that higher pH's of around 5–7 result in the treated waters, several hours are required to achieve an adequate release of chlorine dioxide from the compositions and thus sanitize the water appropriately. As such, it is envisioned that compositions encompassed by the present invention should produce in the quantity of water treated, a pH of from about 3 to about 4. However, lower pH's may be produced in the treated water, if taste characteristics are not important for the intended use.

As documentation that the water treatment compositions of the present invention should preferably produce in the quantity of water treated a pH of about 3 to 4, several experiments were performed. First, an experiment was performed to document that sodium chlorite (UV absorption maxima at 260–270 nm) in an aqueous environment of citric acid (pH 3.5), decomposes and forms chlorine dioxide (UV absorption maxima 340–360 nm). In FIG. 1, the results of the experiment are provided, however, the actual absorbance for each measured component is not indicative of an actual content in the test solution, as their respective extinction coefficients substantially differ:

| Compound | Abs. max | Ext. coeff. |
| --- | --- | --- |
| $NaClO_2$ | 260–270 nm | 140 $M^{-1}cm^{-1}$ |
| $ClO_2$ | 230–360 nm | 1175 $M^{-1}cm^{-1}$ |

The data in FIG. 1 shows rather fast decomposition of $NaClO_2$ at the shown pH and prolonged formation of $ClO_2$. Compositions encompassed hereby which produce a similar pH, it is assumed would also possess similar kinetics of $ClO_2$ formation.

We also performed an experiment to test the effect of pH on the decomposition of sodium chlorite to chlorine dioxide. In the experiment, pH change was achieved by continuous additions of 0.1 ml of 0.05 N HCl to 10 ml of 100×diluted DURA-KLOR®, labelled as 6% chlorine dioxide solution. UV scanning was made within 5 minutes after achieving the shown pH. The same was from 360 nm to 200 nm on Beckman DU-7 spectrophotometer. Results are shown in Table I and in FIG. 2.

TABLE I

THE EFFECT OF pH ON $NaClO_2$ DECOMPOSITION TO $ClO_2$

| Equivalents of HCl added | pH | Abs max (nm) | Abs. at Max | Abs. (nm) | A |
| --- | --- | --- | --- | --- | --- |
| 0 | 9.28 | | 1.49 | 0 | 0 |
| 0.05 | 7.78 | 276.5 | 1.46 | 0 | 0 |
| 0.10 | 7.13 | 276.0 | 1.44 | 0 | 0 |
| 0.15 | 6.75 | 276.5 | 1.42 | 0 | 0 |
| 0.20 | 6.35 | 275.0 | 1.38 | 0 | 0 |
| 0.25 | 3.87 | 275.5 | 1.36 | 355 | 0.24 |
| 0.30 | 3.09 | 275.0 | 1.28 | 355 | 0.32 |
| 0.35 | 2.81 | 274.5 | 1.21 | 355 | 0.38 |
| 0.40 | 2.63 | 273.0 | 1.14 | 355 | 0.42 |
| 0.45 | 2.53 | 272.0 | 1.07 | 355 | 0.58 |

TABLE I-continued

THE EFFECT OF pH ON NaClO$_2$ DECOMPOSITION TO ClO$_2$

| Equivalents of HCl added | pH | Abs max (nm) | Abs. at Max | Abs. (nm) | A |
|---|---|---|---|---|---|
| 0.50 | 2.43 | 272.5 | 1.02 | 355 | 0.62 |
| 0.55 | 2.63 | 271.0 | 0.95 | 355 | 0.68 |

Figure 2:
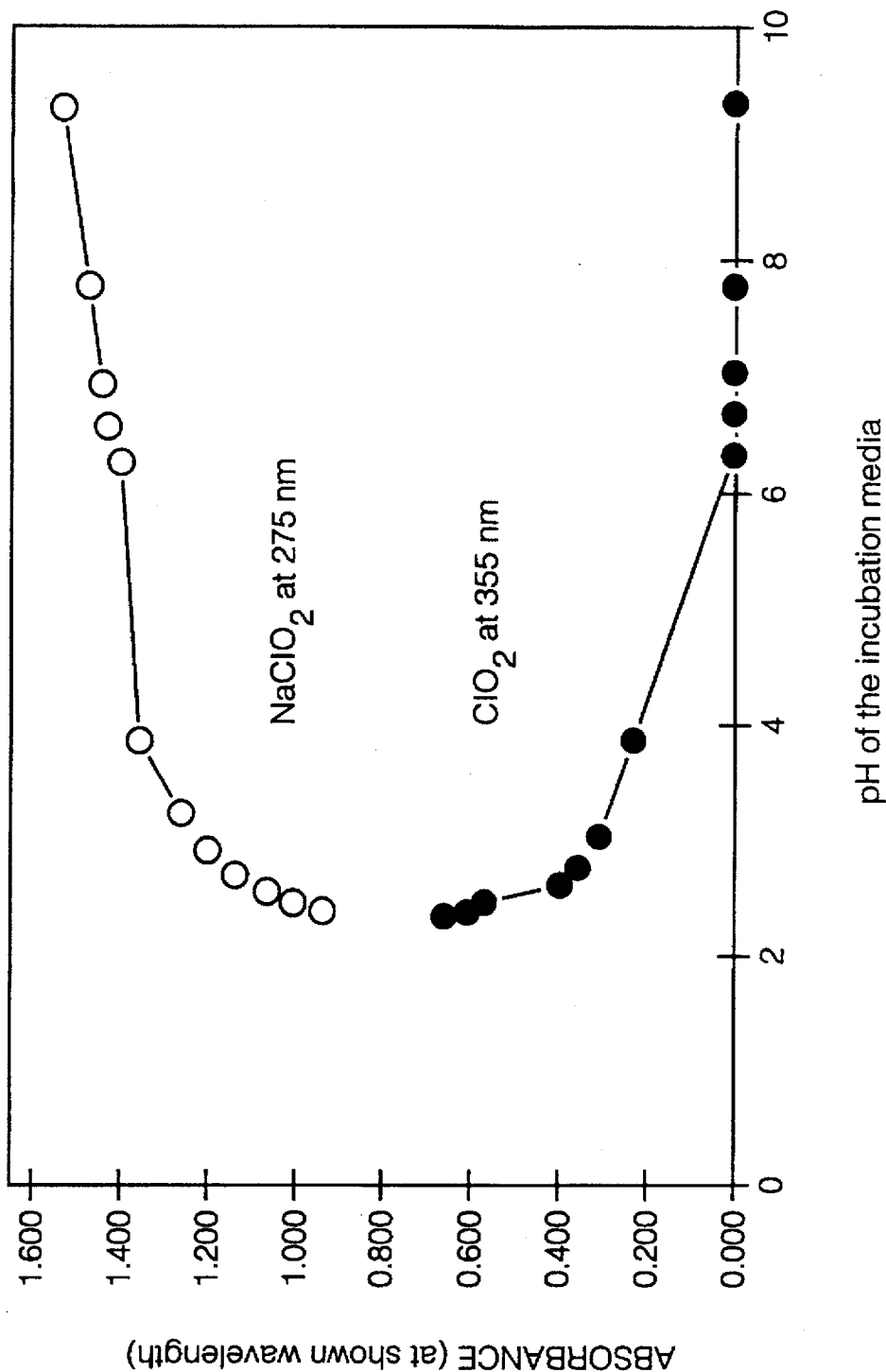
FIG. 2—Shows the effect of pH on sodium chlorite decomposition to chlorine dioxide.

As may be seen upon review of Table I and FIG. 2, the peak of ClO$_2$ shows (within 5 minutes) first at pH 3.87 and continuously raises with reduced pH of the medium. Therefore, the inventors postulated that a suitable water sanitation tablet when completely dissolved should adjust the pH of the contaminated water optimally to about pH 3–4.

In order to produce one liter of treated water using one or more of the present inventive compositions, it is preferable that the pH of the Liter of water be reduced to about 3–4 after treatment, and that a sufficient amount of chlorine dioxide be produced in the treated water to suitably disinfect/sanitize the same. Generally, it is believed that the combination of about 400 to 600 mg of citric acid, anhydrous USP and about 15 to 25 mg of sodium chlorite, anhydrous meet these requirements. However, such values are not limiting to the present invention, since it is only necessary that the resulting water be suitably sanitized.

Additionally, it should be understood that since different "acid activators" may possess different Ka values, different amounts of said "acid activators" may be required in order to achieve a desired pH. Moreover, depending on the initial pH of the water treated, more or less acid activator may be required to reach a desired pH range. Additionally, even though not preferred, one may desire to produce in the treated water a pH of about 2–3 or 5–7, such pH's would necessarily require the use of different amounts of acid activators.

Similarly, it is noted that if an alkaline additive(s) is utilized in the present inventive compositions, this may affect the amount of the "acid activator" needed to effect a given pH. Based on these considerations, it is envisioned that those of ordinary skill in the art will readily understand that an appropriate amount of a "acid activator" may be determined simply, if desired, through the preparation of different compositions containing different amounts of an acid activator(s). Nonetheless, the values given above are exemplary of those suitable to produce compositions encompassed by the present invention.

It is realized, that persons practicing the present invention may wish to disinfect or treat quantities of water much larger than one liter, or conversely smaller than one liter (e.g., 100–500 ml). The above values are provided only as exemplary values, and thus treatment of larger or smaller volumes of water, may require the use of an acid activator in more than or less than a direct proportional amount to that recited above.

Additionally, when activated carbons are utilized in the present inventive compositions, they may affect the amount of the acid activator required to produce a given pH. It should be noted, however, that experiments performed herein clearly indicate that the presence of activated carbons does not affect adversely the formation of chlorine dioxide in the treated water. As a result, it is envisioned that even when activated carbons are present in the inventive compositions, the pH of the treated waters should be preferably around 3–4.

As indicated in the Background Section hereof, a reduction in the level of humic substances in water treatment is often highly desirable. Thus, in addition to the presence of sodium chlorite and an acid activator therefor, the present inventive compositions may also optionally contain activated carbon(s) for the absorption of humic substances occurring in a water sample. Such activated carbon may be impregnated with a metal ion (e.g., $Fe^{+3}$), if so desired.

The inventors hereof have discovered that certain ion impregnated activated carbons are extremely efficient and valuable in removing humic substances from water samples. For example, activated carbons impregnated with an ion such as $Fe^{+3}$ in an amount of about 0.5 to 15% w/w based on the weight of the final absorbent can effectively and easily be used to remove humic substances from a water sample.

Activated carbons and ion-impregnated activated carbons when utilized in the compositions herein described are preferably in a powdered or granular form. However, activated carbons can be spatially separate from the present inventive compositions and still be used in the present inventive methods. Moreover, the inventive water treatment kits herein provided can advantageously contain a spatially separate activated carbon component, if so desired. When an activated carbon component is spatially separate from the compositions herein provided, it is thought preferable that it should exist in the form of a fabric, a fleece, or in a granular form in a tea-bag like configuration. Such forms would allow waters to be effectively treated for humic substances while being easily removed from the water after treatment. Filter pads containing activated carbons can also be utilized if so desired. In such an instance, one would recirculate a water sample through an activated carbon filter, until an acceptable level of humic substances occurred in the sample.

As an example of preparing an ion impregnated activated carbon, the following illustrative preparation is provided wherein an activated carbon absorbent is impregnated with iron (3% w/w).

Exemplary Ion-Impregnated Activated Carbon

An activated carbon absorbent which is impregnated with iron was prepared by impregnation of a fraction of ground granulated active charcoal (AC), size 100–160 microns by a spraying method. As an impregnation solution, the inventors used 0.4M $Fe_2(SO_4)_3 \cdot 9\ H_2O$ in water at a volume equal to the sum of pores volume (1.0 l/kg) of the used AC. The formed substrate was kept at 30° C. in a closed vessel in the incubator. After repeatedly washing the substrate with distilled water (approximately 40 l/kg) until no ferric ions ($Fe^{3+}$) were detected in the extract, the product was dried at 100° C. The content of iron (Fe) was 3.0 weight percent.

The original active charcoal (AC) and the sorbent activated with ferric hydroxide (AC/Fe) were tested for adsorption isotherms, and for kinetics of adsorption of humic acids (HA) from an aqueous solution at 25° C. Test results obtained showed a significant and substantial increase of sorption capacity for the iron impregnated activated charcoal when compared with the original activated charcoal.

The compositions of the present invention are described herein as being stable prior to their intended use. This stability results in part from the inventors' inclusion in the present inventive compositions of a reaction-preventing barrier between the acid activator and the sodium chlorite utilized in the compositions. Suitable barriers include those which are easily amendable to commercial production processes, and yet do not interfere with the release of chlorine dioxide, once the present inventive compositions are introduced into an aqueous environment. Cost considerations may also be an appropriate factor for consideration in deciding what type of barrier should be utilized.

Further to the above, it is only necessary that the barrier which is produced between the acid activator and sodium chlorite in the present inventors' compositions prevent a premature reaction of the two components. Whether this is achieved through the use of a protective coating or a microencapsulation technique, or a separation/segregation technique, is of no importance. It is only necessary that in the inventive compositions that the acid activator and sodium chlorite both exist in the compositions without the ability to prematurely react and release chlorine dioxide. Exemplary of suitable barriers are those provided for in the tablet formulations discussed below. However, these formulations are not limiting to the present invention, since equivalent techniques may be readily understood by those skilled in the art and achieve the objects of the present invention.

Protective coating techniques such as used in the tableting formulations below are believed to be a highly advantageous way to create a reaction preventing barrier in the present inventive compositions. In the tablet formulations encompassed hereby, sodium chlorite (or a premix thereof) is preferably mixed with physiologically acceptable ingredients such as magnesium carbonate, polyvinylpyrrolidone, stearyl alcohol, sodium lauryl sulfate, stearic acid, magnesium stearate, glycine or the like, to form a protective coating on the sodium chlorite before adding an acid activator to the composition being prepared. The use of protective coating techniques to form reaction preventing barriers are especially preferred with respect to tablet, powder and capsule compositions, since such coatings can be formed using commercial mixing procedures and mixing equipment (e.g., V-blenders) which are readily known and/or available to those skilled in the art.

The compositions of the present invention are preferably formulated into a form which can be easily handled, and which may be used advantageously to practice the present inventive methods. Exemplary of such forms would include the following, a tablet, a capsule, a powder, a suspension or a dispersion. It only being necessary that whatever the form chosen, it produce in the treated water the desired pH and appropriately disinfect/sanitize the water, while at the same time remaining stable prior to its intended use. Nonetheless, it is thought preferable if the compositions of the present invention are manufactured into a tablet-like form.

Tablets are thought preferable in the present invention, due to their ease of manufacture, and their ease of use. In this regard, tablets could easily be prepared and placed in a format such as a blisterpack container, if so desired, which includes instructions for practicing the water sanitizing methods of the present invention. Similarly, tablets are thought preferable in the present invention, since those of ordinary skill in the art would realize that this would include the use of effervescent tablets.

If tablets are prepared according to the present invention, suitable excipients may be utilized therein. Exemplary of such excipients are fillers, lubricants, stabilizers, dyes, anticaking agents, and the like. Nonetheless, whatever excipients are utilized in a given tablet formulation, the same should result in a tablet which remains stable until its intended use, and which produces the desired effect in the water to be treated. Of course, all excipients utilized in such a tablet formulation should be physiologically acceptable and should not adversely effect taste characteristics associated with the treated water.

Having described different inventive compositions which are encompassed hereby, the following exemplary formulations are provided as an aid to those skilled in the art practicing the present invention. Each of the following formulations can be utilized to prepare a tablet composition of the present invention. Similar formulations can also be utilized, if desired, to form powders or capsules utilizing readily known techniques.

EXEMPLARY TABLETS COMPOSITIONS

The following water sanitation tablets were formulated and achieve the objects of the present invention, and are thus illustrative of compositions which are encompassed by the present invention, and processes for the manufacture thereof.

TABLET L

| Premix | (20% $ClO_2$): |
|---|---|
| $NaClO_2$ | 20.0% |
| NaCl | 78.2% |
| $Na_2HPO_4$ | 1.8% |
| Each Tablet Containing: | |
| Premix | 115 mg |
| CITRIC ACID | 550 mg |
| PER TABLET FORMULA | |
| A. Premix (20% of $ClO_2$) | 115.00 mg |
| Magnesium carbonate (heavy) | 50.00 mg |
| PVP(polyvinylpyrrolidone-P-6755) | 10.00 mg |
| Stearyl alcohol (powdered) | 10.00 mg |
| B. Sodium bicarbonate | 100.00 mg |
| Citric acid, anhydrous | 450.00 mg |
| Glycine | 4.00 mg |
| Calcium phosphate, monobasic | 3.00 mg |
| TOTAL TABLET WEIGHT = | 742.00 mg |

A. (Mixing Directions):
1. Gently blend the first two ingredients and pass through a #40 sieve. Let air dry in low humidity at least an hour.
2. Add the polyvinylpyrrolidone and blend gently.
3. Powder the stearyl alcohol (#40 sieve) and incorporate into the mixture.
4. V-blend the mixture.

B. (Mixing Directions):
1. Powder the citric acid and sieve (#40).
2. Blend with the other ingredients of B.
3. Place in drying oven at about 40° C. for about two to three hours, then let cool to room temp. in low humidity.
4. Pass through #20 sieve and V-blend with the A. mixture.

The mixture of A and B ingredients is thereafter tableted IN A LOW HUMIDITY area.

TABLET M

| Premix | (20% $ClO_2$): |
|---|---|
| $NaClO_2$ | 20.0% |
| NaCl | 78.2% |
| $Na_2HPO_4$ | 1.8% |
| Each Tablet Containing: | |
| Premix (20% $ClO_2$) | 115 mg |
| CITRIC ACID | 450 mg |

TABLET M-continued

PER TABLET FORMULA

| | |
|---|---|
| A. Premix (20% $ClO_2$) | 115.00 mg |
| Magnesium carbonate (heavy) | 50.00 mg |
| PVP(polyvinylpyrrolidone-P-6755) | 10.00 mg |
| Magnesium stearate | 10.00 mg |
| Sodium lauryl sulfate | 10.00 mg |
| B. Sodium bicarbonate | 100.00 mg |
| Citric acid, anhydrous | 550.00 mg |
| Glycine | 4.00 mg |
| Calcium phosphate, monobasic | 3.00 mg |
| TOTAL TABLET WEIGHT = | 852.00 mg |

A. (Mixing Directions):

1. Gently blend the first two ingredients and pass through a #40 sieve. Let air dry in low humidity at least an hour.
2. Add the polyvinylpyrrolidone and blend gently.
3. Add the magnesium stearate and sod. laur. sulfate (#40 sieve) and incorporate into the mixture.
4. V-blend the mixture.

B. (Mixing Directions):

1. Powder the citric acid and sieve (#40).
2. Blend with the other ingredients of B.
3. Place in drying oven at about 40° C. for about two to three hours, then let cool to room temp. in low humidity.
4. Pass through #20 sieve and V-blend with the A mixture.

The mixture of A and B ingredients is thereafter tableted IN A LOW HUMIDITY area.

TABLET S

| Premix | (20% $ClO_2$): |
|---|---|
| $NaClO_2$ | 20.0% |
| NaCl | 78.2% |
| $Na_2HPO_4$ | 1.8% |

| Each Tablet Containing: | |
|---|---|
| Premix (20% $ClO_2$) | 115 mg |
| IMPREGNATED ACTIVE CARBON | 15 mg |
| CITRIC ACID | 550 mg |

PER TABLET FORMULA

| A. | | For 150 |
|---|---|---|
| Sodium bicarbonate | 100.00 mg | 15.00 g |
| Mannitol powder | 40.00 mg | 6.00 g |
| Binder solution (wt. contribution) | 46.00 mg | 6.90 g |
| PVP(polyvinylpyrrolidone-P-6755) | 30.00 mg | 4.50 g |
| Magnesium carbonate (heavy) | 30.00 mg | 4.50 g |
| | | (36.90 g) |
| B. | | |
| Premix (20% $ClO_2$) | 115.00 mg | 17.25 g |
| Impregnated active carbon | 15.00 mg | 2.25 g |
| Citric acid, anhydrous | 550.00 mg | 82.50 g |
| Stearic acid | 10.00 mg | 1.50 g |
| Magnesium stearate | 10.00 mg | 1.50 g |
| Sodium lauryl sulfate | 7.00 mg | 1.05 g |
| Glycine | 7.00 mg | 1.05 g |
| TOTAL TABLET WEIGHT = | 960.00 mg | |

A. (Mixing Directions):

1. Gently blend the (A) ingredients making a wet granulation using the binder solution and sieve #20.
2. Dry in oven at 50° C. for about two hours.
3. Sieve #20 the dry granulation. (May rework fines if necessary).

B. (Mixing Directions):

1. Mix the stearic acid, magnesium stearate, sodium lauryl sulfate and the glycine.
2. Add to this mixture the impregnated active carbon and mix well.
3. Add the Premix and the citric acid, anhydrous (sieve #20) to this mixture and mix well.
4. Add this mixture (B) to the granulation (A) and V-blend the final mixture.

Tablet at this stage IN LOW HUMIDITY area using 9/16 standard concave punch/die. Thereafter, preferably strip-wrap package in foil lined air-tight wrap.

[1]BINDER SOLUTION FORMULATION

| Per Tablet Amounts: | |
|---|---|
| Acacia powder, U.S. P. | 12.000 mg |
| Gelatin | 34.000 mg |
| Distilled water q.s. ad | 0.157 mL |
| WEIGHT CONTRIBUTION PER TABLET = | 46.0 mg |

EVALUATION OF TABLET FORMULATIONS

The effects produced by the addition of tablet formulations L and M upon addition to 100 mL of untreated water (inoculated with $2.5 \times 10^6$ E. coli/ml) are shown in Table II below.

TABLE II

| Parameter Studied | Tablet L | Tablet M |
|---|---|---|
| Rate of disintegration at 20% (in seconds) | 55 ± 4 | 132 ± 11 |
| Residues: | | |
| visible, insoluble chemicals | none residual $NaClO_2$ | none residual $NaClO_2$ |
| pH | 3.55 | 3.47 |
| Color | clear water | clear water |
| Smell | none | none |
| Bactericidal (E. coli)* Effect (% kill) in 1 tablet in: | | |
| 5 min. | 100% | 100% |
| 10 min. | 100% | 100% |
| 15 min. | 100% | 100% |
| 30 min. | 100% | 100% |
| Effect (% kill) in 3 tablets in: | | |
| 5 min. | 100% | 100% |
| 10 min. | 100% | 100% |
| 15 min. | 100% | 100% |
| 30 min. | 100% | 100% |

*Starting inoculation was $2.5 \times 10^6$ E. coli/ml.

Figure 3:
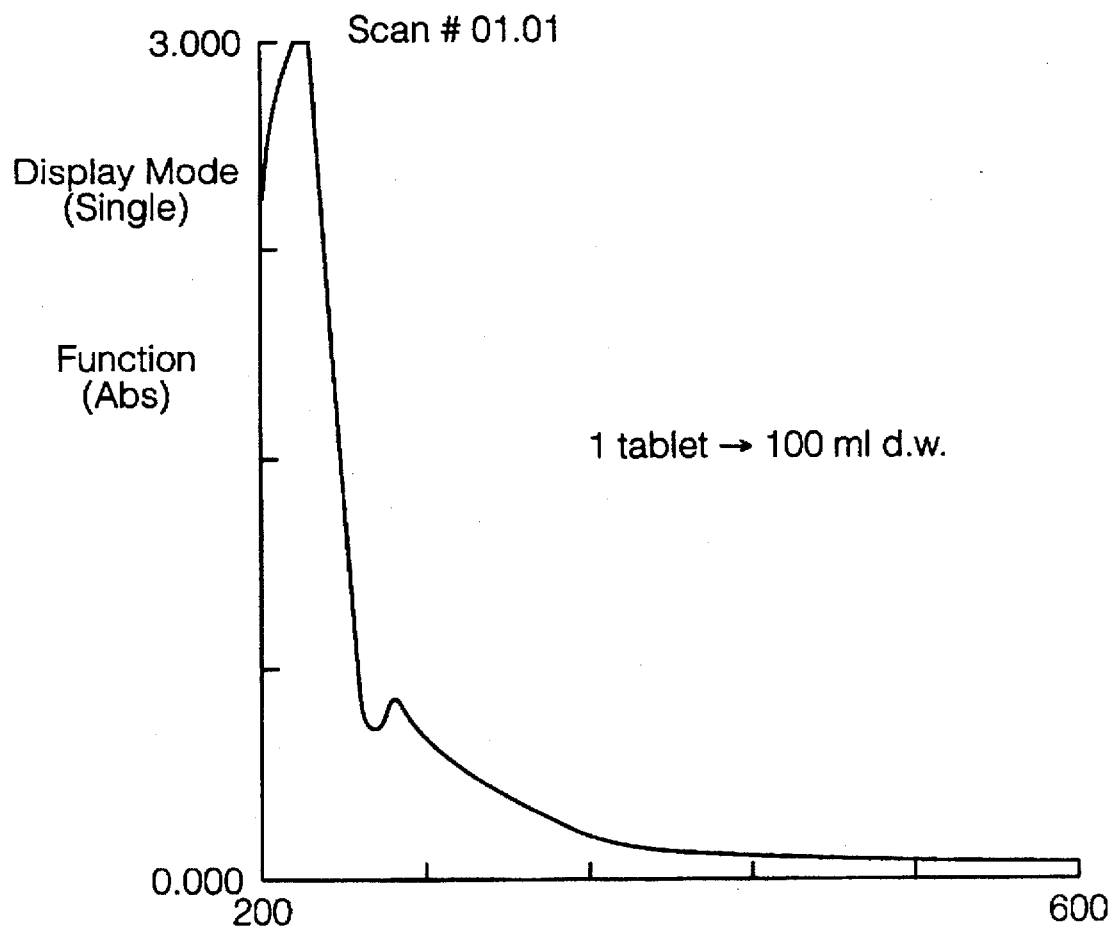
FIG. 3—UV spectra of Tablet Formulation L in water.
Figure 4:
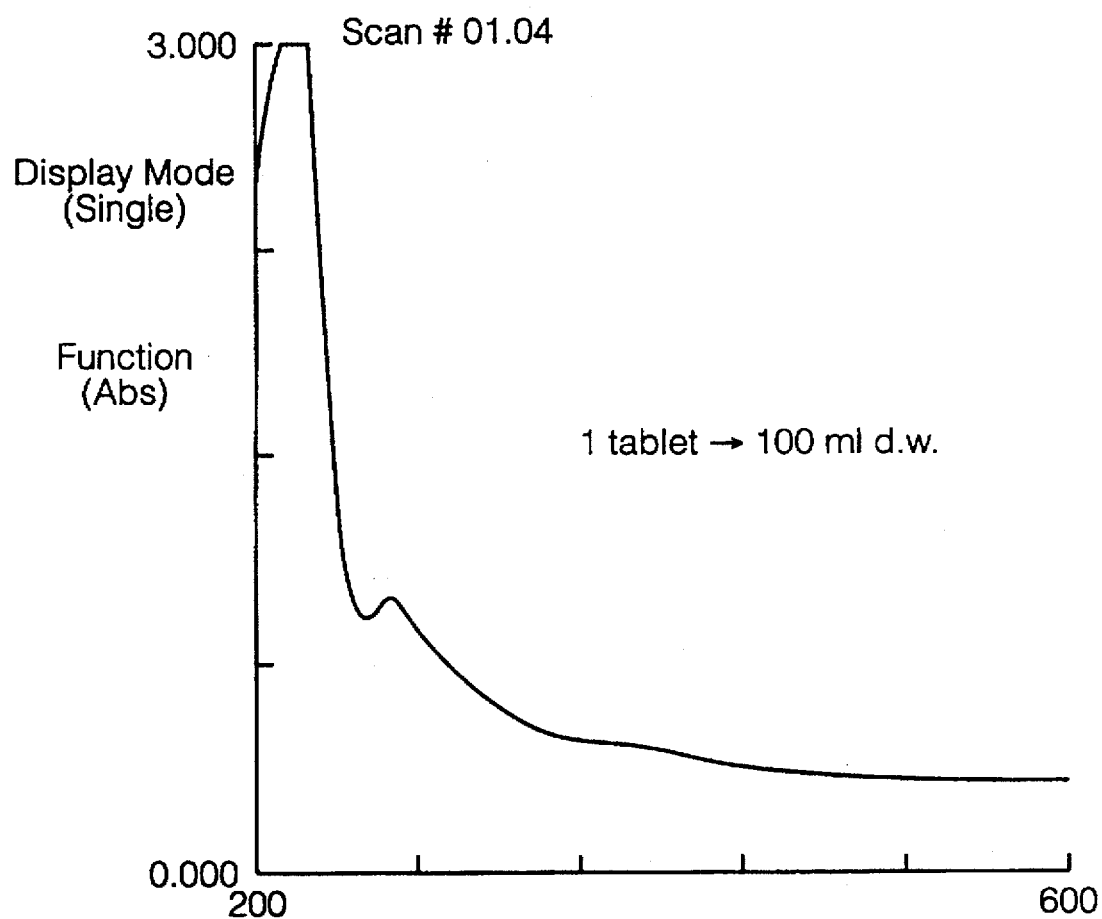
FIG. 4—UV spectra of Tablet Formulation M in water.

Results shown in Table II show that both tablet formulations L and M were 100% effective within 5 minutes without producing any adverse or objective or visual changes in the E. coli contaminated water. Additionally, in FIGS. 3 and 4 hereof, there are shown respectively, UV Spectra 200–600 nm of the formulations L and M at 10–30 minutes after solubilization of the respective tablets. As seen in FIGS. 3 and 4, absorbance maximums occur at 258 nm indicating the presence of chlorine dioxide in each of the treated water samples. While the above tablet formulations L and M document the high effectiveness of the formulations herein which contain an active component (sodium chlorite) and an acid activator (citric acid), tablet formulation S is also provided to evidence the effectiveness of tablet formulations encompassed hereby which also contain therein an active carbon absorbent.

Additionally, while Formulations L and M were initially developed for bacteria contaminated tap waters, Formulation S was developed for waters also contaminated by organic compounds, such as humic acids, etc. Nonetheless, initially it was realized that the presence of a strong absorbent therein might interfere with the effectiveness of the sterilization system ($NaClO_2$—citric acid) by adsorbing the starting materials or the developed chlorine dioxide. As such, the efficacy of tablet Formulation S was tested as follows.

E. coli stain was pipetted into 1 Liter of distilled water to form approximately $10^8$ bacteria/ml. One tablet or half a tablet was added to test the effectiveness and aliquots of the bacterial resorption before and 5, 10, 15 and 30 minutes after adding tablet S were taken and placed on agar plates. The bacterial growth as Colony Forming Units were read after 24 hours of incubation at 37° C. Results are provided in Table III.

TABLE III

Tablet Formulation S

| Time(min) | 1 tablet/1 L | 1 tablet/2 L |
|---|---|---|
| 0 | massive growth* | massive growth* |
| 5 | 0 | 0 |
| 10 | 0 | 0 |
| 15 | 0 | 0 |
| 30 | 0 | 0 |

*not possible to count, most of the plate was covered with a thin white layer of outgrowth.

Based on results contained in Table III, it can be seen that Formulation S at both concentrations (1 tablet per 1 or 2 Liters of contaminated water) completely killed all bacteria at 5 minutes. This study documents that the presence of the absorbent does not interfere with the bactericidal effect of the active components.

While the tablets and other compositions provided herein remain stable prior to their introduction into an aqueous environment, it is thought preferred that the formulations used to prepare such compositions, and moreover, the compositions themselves be maintained and stored under low humidity conditions. In the case of tablet composition, it is thought preferred that the tablets be provided in a container which can maintain the composition in a low humidity environment. For example, the tablets could be provided in a humidically-sealed container such as in a blisterpack arrangement, or even in a bottle type container in combination with a desiccant packet, etc. The ability to manufacture and thereafter store tablets and similar compositions under low humidity conditions is readily understood by those skilled in the art; thus such considerations do not limit the present discovery.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred herein above are expressly incorporated herein by reference in their entirety.

REFERENCES

1. E. M. Aieta and J. D. Berg, "A Review of Chlorine Dioxide in Drinking Water Treatment", Journal AWWA, pp. 62–72, June 1986.
2. B. W. Lykins, J. A. Goodrich and J. C. Hoff, "Concerns with using chlorine-dioxide disinfection in the USA", J. Water SRT-Aqua, Volume 39, No. 6, pp. 376–386, 1990.
3. Kalavská D., Holoubek J.:Analýza vôd. Alfa, Bratislava, 1989.
4. Žáček L.:Huminové látky v přirozených vodách a možnosti jejich odstraňování. Works and studies VUV, Prague, 1976.
5. Šorm J., Žáček L., Využití spektroskopichý metod k hodnocení organického znečistění při procesech úpravy vody. Publication VUV, No. 16, SZN, Prague 1987.
6. Havlík B., Hanušová J.: Vodní hospodářstvi No. 4, 85 (1989).
7. Žáček L.: Vodní hospodářstvi No. 1, 5 (1989).
8. Vágner V., Janda V., Havel L., Rudovský J.: Vodní hospodářství No. 12, 315 (1989).
9. Horáková M., Lischke P., Grünwald A.: Chemické a fyzikální metody analýzy vod. SNTL, Prague 1986.

What is claimed is:

1. A composition for the treatment of water comprising sodium chlorite, an acid activator, and a reaction-preventing barrier for separating said sodium chlorite and said acid activator wherein said reaction-preventing barrier comprises a protective coating on the sodium chlorite and said composition remains stable prior to introducing the composition into the water.

2. The composition of claim 1, wherein said acid activator is citric acid or citric acid, anhydrous.

3. The composition of claim 1, further comprising an activated carbon.

4. The composition of claim 1 further comprising an ion impregnated activated carbon.

5. The composition of claim 4 in the form of a tablet.

6. The composition of claim 4, wherein the ion impregnated activated carbon is impregnated with an iron ion.

7. The composition of claim 1 is in the form of a tablet.

8. The composition of claim 1 is in the form of a powder.

9. The composition of claim 1 is in the form of a capsule.

10. The composition of claim 1 wherein said reaction-preventing barrier further comprises a protective coating on the acid-activator.

11. The composition of claim 1 comprising a residual moisture content of an amount below about 2–3% w/w.

12. A composition for the treatment of water to produce drinking water, the composition comprising sodium chlorite, an acid activator and a reactive-preventing barrier for separating the sodium chlorite and the acid activator and maintaining the stability of the composition wherein the reaction-preventing barrier is a protective coating formed of components selected from the group consisting of magnesium carbonate, polyvinylpyrrolidone, stearyl alcohol, sodium lauryl sulfate, stearic acid, magnesium stearate and glycine.

13. A composition for the treatment of water comprising sodium chlorite, an acid activator, and a reaction-preventing barrier for separating said sodium chlorite and said acid activator wherein said reaction-preventing barrier comprises a protective coating on the acid activator and said composition remains stable prior to introducing the composition into the water.

14. The composition of claim 13 wherein said acid activator is citric acid or citric acid, anhydrous.

15. The composition of claim 13, further comprising an activated carbon.

16. The composition of claim 13, further comprising an ion impregnated activated carbon.

17. The composition of claim 16 wherein the ion impregnated activated carbon is impregnated with an iron ion.

18. The composition of claim 16 is in the form of a tablet.

19. The composition of claim 13 is in the form of a tablet.

20. The composition of claim 13 is in the form of a powder.

21. The composition of claim 13 is in the form of a capsule.

22. The composition of claim 13 comprising a residual moisture content of an amount below about 2–3% w/w.

23. A composition for the treatment of water comprising sodium chlorite, an acid activator, a reaction-preventing barrier for separating said sodium chlorite and said acid activator, and an ion impregnated activated carbon, wherein said ion impregnated activated carbon is impregnated with an iron ion and said composition remains stable prior to introducing the composition into the water.

* * * * *